United States Patent [19]
Swerdloff et al.

[11] Patent Number: 5,548,627
[45] Date of Patent: Aug. 20, 1996

[54] RADIATION THERAPY SYSTEM WITH CONSTRAINED ROTATIONAL FREEDOM

[75] Inventors: Stuart Swerdloff; Thomas R. Mackie; Timothy Holmes, all of Madison, Wis.

[73] Assignee: Wisconsin Alumni Research Foundation, Madison, Wis.

[21] Appl. No.: 71,742

[22] Filed: Jun. 9, 1993

Related U.S. Application Data

[63] Continuation-in-part of Ser. No. 854,521, Mar. 19, 1992, Pat. No. 5,317,616.

[51] Int. Cl.$^6$ .................................................. H05G 1/60
[52] U.S. Cl. ................................... 378/4; 378/19; 378/65
[58] Field of Search ...................................... 378/65, 19, 4

[56] References Cited

U.S. PATENT DOCUMENTS

| | | | |
|---|---|---|---|
| 4,233,519 | 11/1980 | Coad | 250/514 |
| 4,660,799 | 4/1987 | Butland | 248/676 |
| 4,754,147 | 6/1988 | Maughan et al. | 250/505.1 |
| 4,794,629 | 12/1988 | Pastyr et al. | 378/152 |
| 4,817,125 | 3/1989 | Sklebitz | 378/152 |
| 4,868,843 | 9/1989 | Nunan | 378/152 |
| 4,868,844 | 9/1989 | Nunan | 378/152 |
| 4,905,268 | 2/1990 | Mattson et al. | 378/158 |
| 4,987,309 | 1/1991 | Klasen et al. | 250/492.1 |
| 4,998,268 | 3/1991 | Winter | 378/63 |
| 5,012,506 | 4/1991 | Span et al. | 378/152 |

FOREIGN PATENT DOCUMENTS

| | | |
|---|---|---|
| 0037008 | 3/1981 | European Pat. Off. . |
| 0113879 | 12/1983 | European Pat. Off. . |
| 0464645A1 | 1/1991 | European Pat. Off. . |
| 2023648 | 8/1970 | France . |
| 2346754 | 10/1977 | France . |
| 519887 | 3/1977 | Russian Federation ........ 378/65 |
| 553766 | 11/1977 | Russian Federation ........ 378/65 |

OTHER PUBLICATIONS

Calculation and Application of Point Spread Functions for Treatment planning with High Energy Photon Beams, *Acta Oncologica* 26 (1987) pp. 49–56, A. Ahnesjo, et al.

Methods of Image Reconstruction from Projections Applied to Conformation Radiotherapy, *Phys. Med. Biol.*, 1990, vol. 35, No. 10, 1423–1434, Bortfeld, et al.

Feasibility Solutions in Radiation Therapy Treatment Planning, *Dept. of Radiation Therapy*, Univ. of PA School of Med., pp. 220–224, Altschuler, et al. (1984).

A Primer on Theory & Operation of Linear Accelerators in Radiation Therapy, *Medical Physics Pub. Corp.*, (1981) C. J. Karzmark, et al.

The Accuray Neutron 1000, A Medical Systems for Frameless Stereotoxic Radiosurgery, Accuray, Inc., J. R. Adler, et al., May 1992.

Optimization of Stationary and Moving Beam Radiation Therapy Techniques, *Radiotherapy and Ocology*, 12 (1988) 129–140, A. Brahme.

A Unified Approach to the Optimization of Brachytherapy and External Beam Dosimetry, *Int. J. Radiation Ocology Biol. Phys.*, vol. 20 pp. 859–873, Holmes, et al. (1991).

(List continued on next page.)

*Primary Examiner*—Craig E. Church
*Attorney, Agent, or Firm*—Quarles & Brady

[57] ABSTRACT

A radiation therapy machine has a constrained angular freedom to produce a beam only within a gantry plane. A radiation shield may be stationary and not attached to the gantry or rotating to always block the primary beam. The constrained motion reduces the risk of patient/gantry collision and provides for extremely accurate radiation therapy planning. The therapy machine, so constrained, may include a tomographic imaging system on a single gantry. The two systems cooperate and employ many of the same hardware components to both plan and carry out therapy sessions in which irregularly shaped treatment volumes are accurately irradiated while tissue surrounding those volumes is minimally irradiated.

5 Claims, 11 Drawing Sheets

OTHER PUBLICATIONS

Optimization by Simulated Annealing of Three-Dimensional Conformal Treatment Planning for Radiation Fields Defined by a Multileaf Collimator, *Phys. Med. Biol.*, 1991, vol. 36, No. 9, 1201–1226, S. Webb.

Optimization of Conformal Radiotherapy Dose Distributions by Simulated Annealing, *Phys. Med. Biol.*, vol. 34, No. 10, 1349–1370, S. Webb (1989).

A Constrained Least–Squared Optimization Method for External Beam Radiation Therapy Treatment Planning, *Med. Phys.* 11 (5), Sep/Oct 1984 pp. 659–664, G. Starkschall.

On the Use of Cimmino's Simultaneous Projections Method for Computing a Soulution of the Inverse Problem in Radiation Therapy Treatment Planning, *Inverse Problems*, 4 (1988) 607–623, Y. Censor, et al.

Tomotherapy: A New Concept for the Delivery of Conformal Radiotherapy using Dynamic Compensation, Jul. 1992, Swerdloff, et al.

Progress in Medical Radiation Physics vol. 2, 1985, added by Colin Orton, Plenum Press, W. A. Jennings pp. 1–111.

RADIATION THERAPY SYSTEM WITH CONSTRAINED ROTATIONAL FREEDOM

This invention was made with United States Government support awarded by the National Institute of Health (NIH), Grant Nos. NCI R29 CA48902 and NIH Training Grant NRSA CA09206. The United States Government has certain rights in this invention.

FIELD OF THE INVENTION

This application is a continuation in part of a patent application Ser. No. 07/865,521 filed Mar. 19, 1992, now U.S. Pat. No. 5,317,616 entitled *"Method and Apparatus for Radiation Therapy"*.

This invention relates generally to radiation therapy equipment for the treatment of tumors, or the like, and specifically to a radiation therapy machine having reduced freedom of angular rotation.

DESCRIPTION OF THE ART

Medical equipment for radiation therapy treats tumorous tissue with high energy radiation. The dose and the placement of the dose must be accurately controlled to ensure both that the tumor receives sufficient radiation to be destroyed, and that damage to the surrounding and adjacent non-tumorous tissue is minimized.

External-source radiation therapy uses a radiation source that is external to the patient, typically either a radioisotope, such as $^{60}Co$, or a high energy x-ray source, such as a linear accelerator. The external source produces a collimated radiation beam directed along an axis of radiation toward a tumor site. Although external-source radiation therapy avoids the disadvantages of surgically invasive procedures, it undesirably but necessarily irradiates a significant volume of non-tumorous healthy tissue within the path of the radiation beam as the beam passes through the patient to the tumor site.

The adverse effect of irradiating healthy tissue may be reduced, while maintaining a given dose of radiation in the tumorous tissue, by projecting the radiation beam into the patient along a variety of radiation axes with the beams converging on the tumor site. As a radiation beam is directed along a plurality of radiation axes the particular volume elements of healthy tissue along the path of the radiation beam change, reducing the total dose to each such element of healthy tissue during the entire treatment.

Beams may be directed toward a tumor along a variety of radiation axes in three dimensions. By directing the radiation beam toward the tumor site at different angles in three dimensions, the tumor site is "crossfired" from the largest possible number of directions and the individual voxels of healthy tissue traversed by the radiation beam receive a low dose of radiation.

The irradiation of healthy tissue is also reduced by tightly collimating the radiation beam to the general cross section of the tumor taken perpendicular to the axis of radiation. Numerous systems exist for producing such a circumferential collimation, some of which use multiple sliding shutters which, piecewise, may generate a radio-opaque mask of arbitrary outline.

The treatment of tumors that are convex in a single plane may be performed in a simple manner by restricting the different radiation axis of the beam to angles within that plane. For such tumors, a single rotation of the radiation source about a suitable rotation axis can adequately irradiate the tumor. However, a conventional system constraining the radiation axis to a single plane is inadequate to irradiate tumors that are concave within a rotation plane (which is usually the case).

Thus, multiply articulated radiation sources are generally preferred because of their unconstrained ability to irradiate tumors from virtually any angle thereby minimizing irradiation of individual voxels of healthy tissue and allowing tumors that are convex in a single plane to be targeted in that plane regardless of the plane's spatial orientation.

It is important to limit scattered, uncontrolled radiation in a therapy area. Uncontrolled radiation can scatter off therapy equipment and back into a patient or operator. Radiation scatter from a multiply articulated source requires a protective barrier which is at all times opposed to the radiation source, the patient being disposed between the source and barrier. Ideally, the primary protective barrier absorbs the unattenuated x-rays passing through the patient. With a multiply articulate source, the primary barrier must be moveable to assume any angle directly opposed to the radiation source.

SUMMARY OF THE INVENTION

The present invention provides an improved architecture for radiation therapy equipment in which the motion of the radiation source is constrained to a single plane. This single plane configuration provides a number of benefits over the multiply articulated systems.

Specifically, the present invention employs a gantry rotating within a gantry plane about a table near its axis of rotation. A radiation source is attached to the gantry for directing a radiation beam, including a plurality of rays, toward the patient during its rotation. A compensator positioned between the radiation source and the patient intercepts the beam and independently controls the intensity of each ray according to a control signal based on the gantry angle and the position of the translation table.

It is a first object of the invention to provide a radiation therapy system that is readily adapted to high accuracy radiation planning techniques. By treating the patient on a slice-by-slice basis with radiation directed at angles within a single plane, and by controlling the intensity of each ray of the radiation as a function of angle, tumors of arbitrary shape can be accurately irradiated.

The gantry and radiation source may be enclosed within a torroidal housing embracing the swept volume of the gantry. This configuration helps ensure that the table or patient or operators remain out of the path of the rotating radiation source. A primary barrier may be positioned for rotation within the gantry diametrically opposed to the radiation source. The primary barrier intercepts and occludes radiation as the radiation exits the patient. The torroidal housing of the gantry may also be constructed with materials providing scatter shielding to be used as a stationary secondary barrier to limit scatter radiation within a therapy area. Because the secondary barrier need not rotate with the radiation source, the secondary barrier may be heavier and more effective.

In one embodiment, the gantry rotates continuously as the tumor is translated along the axis of rotation so that a volume of arbitrary length may be treated. The compensator is controlled as a function of both gantry angle and table position.

It is thus another object of the invention to employ the simplified architecture of the present invention in a manner that provides for smooth irradiation of volumes extending along the axis of rotation and wider than the radiation beam. As will be described in detail below, the resultant helical path of the changing radiation axis produced by the continuous rotation of the gantry and simultaneous table motion smooths the irradiated field reducing "gaps" or "hot spots" in the irradiated field.

In addition, helical scanning improves the speed of treatment by eliminating the need to accelerate and decelerate the patient for repositioning between 360° rotations of the gantry such as might be required if the patient were treated along a series of distinct slices perpendicular to the axis of rotation and separated along the axis of translation.

In another embodiment, the gantry may support not only a radiation source for radiation therapy, but also a low energy x-ray source and an opposed detector array for acquiring data for computerized tomographic reconstructions as the gantry rotates.

It is yet another object of the invention to decrease the time and improve the accuracy of both therapy planning and therapy sessions so that both planning and therapy may be conducted in short succession. By reducing the freedom of movement of the radiotherapy system to a single plane there is improved correlation between the data generated by the tomographic imaging system and the data necessary to control the radiation therapy system. The similar geometries of the two systems permit their effective combination.

The tomographic images developed by the CT machine may provide the necessary data to produce signals to control the compensator. In one embodiment, the therapist identifies the tumor directly with reference to the tomographic image.

By having the tomographic imaging system and radiation therapy system on a common gantry, a new tomographic image can be produced each time a patient is to receive treatment. The radiologist can view and use the image to adjust therapy protocol while a patient remains on the translation table.

Yet another object of the invention is to provide a method of tracking the position of the tumor during therapy and stopping a therapy session if the tumor is in an unanticipated position. The CT machine provides images of the patient that can be related to the image generated during treatment planning. If the patient moves, the mechanism can automatically turn off the radiation source or alert a therapist of the movement.

The foregoing and other objects and advantages of the invention will appear from the following description. In the description, reference is made to the accompanying drawings which form a part hereof and in which there is shown by way of illustration several preferred embodiments of the invention. Such embodiments do not necessarily represent the full scope of the invention, however, and reference must be made therefore to the claims herein for interpreting the scope of the invention.

DESCRIPTION OF THE PREFERRED EMBODIMENT

Figure 1:
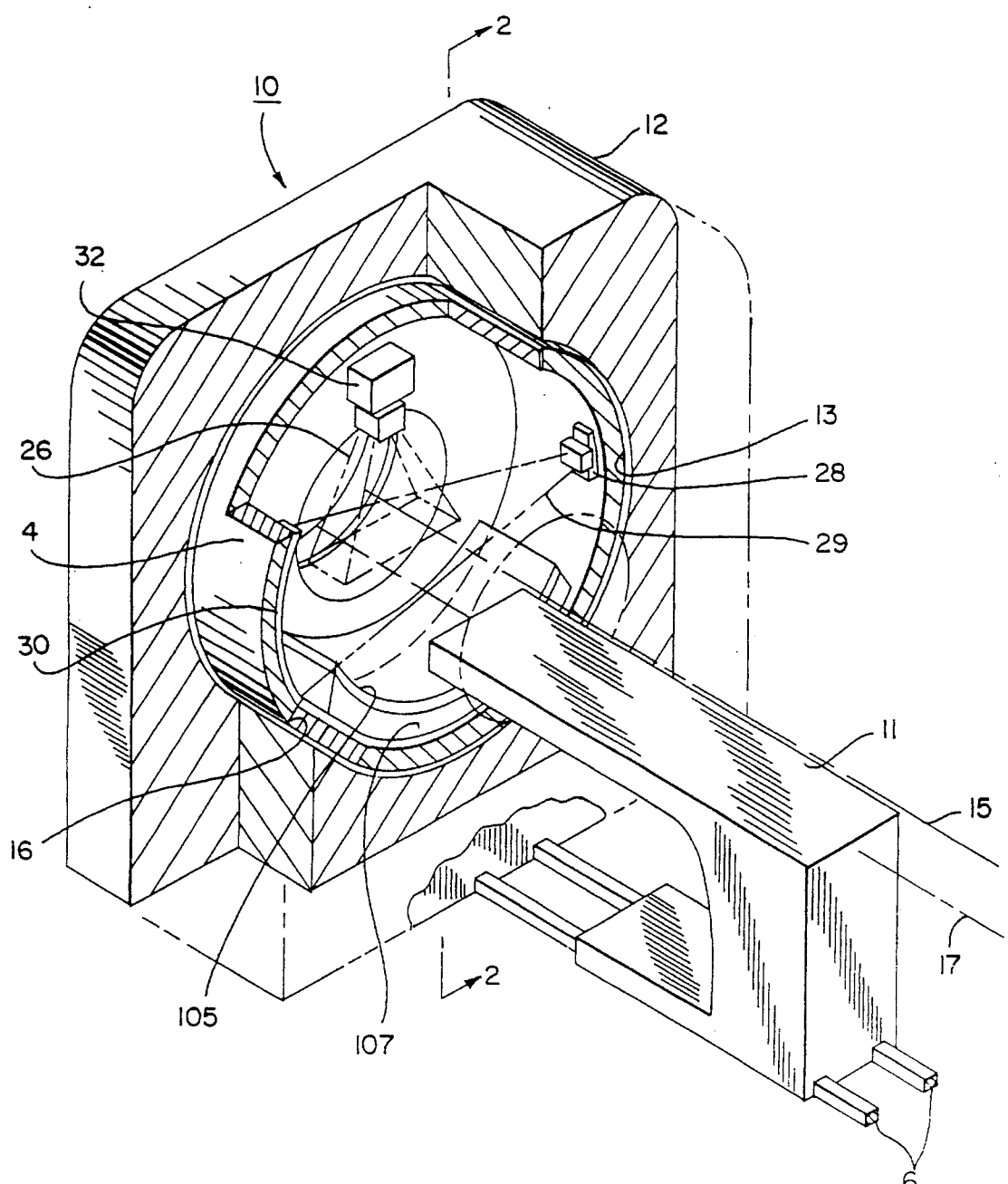
FIG. 1 is a view in partial section of the radiation therapy machine of the present invention.

Referring to FIG. 1, a radiation therapy machine 10 embodying the present invention includes, a stationary, generally block shaped radiation barrier 12 constructed of a dense concrete or other suitable radiation attenuating material. A cylindrical bore 13 centered on horizontal bore axis 15 passes through the front and rear surfaces 24 and 25 of the barrier 12.

A table 11 disposed along a translation axis 17 may slide along that axis 17 through the bore 13 passing first the front surface and then the rear surface 25. The table 11 is supported along guide tracks 6 and moved by a motorized drive, such as is well known in the art, so that its position may be controlled by a computer as will be described.

Figure 2:
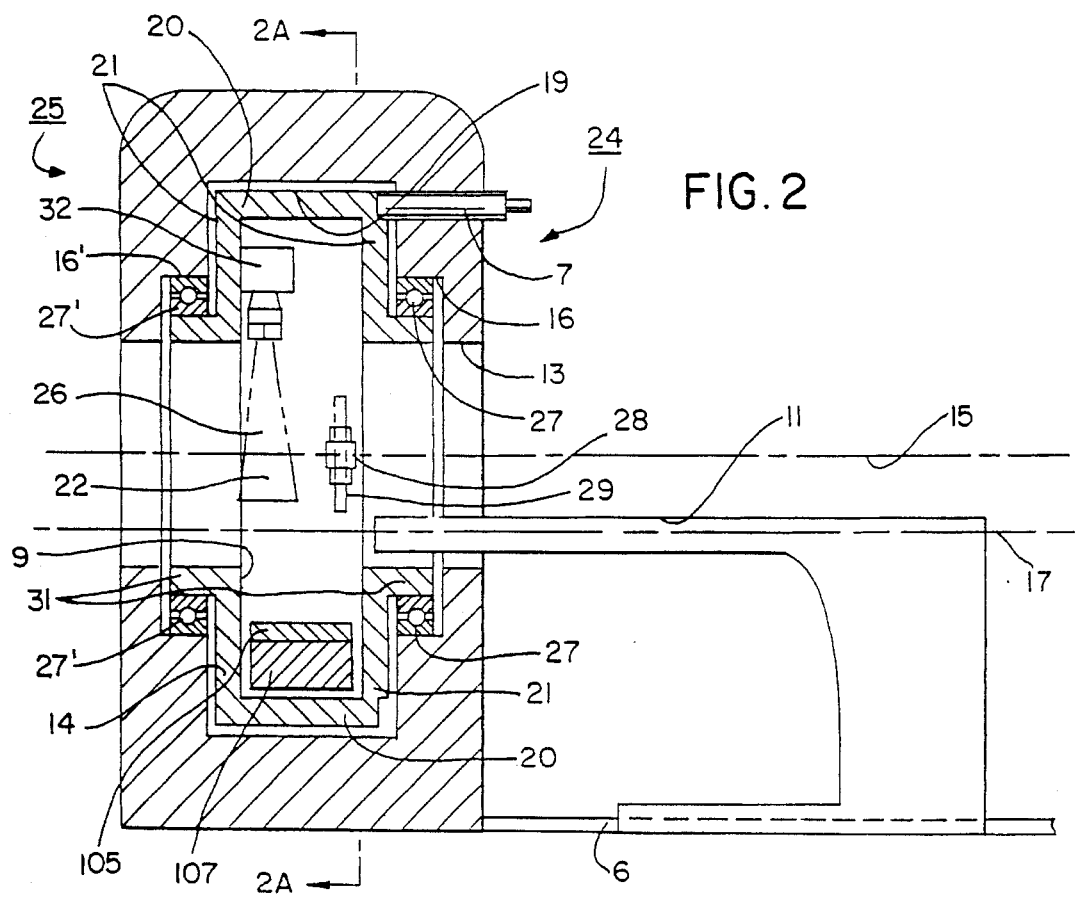
FIG. 2 is a cross sectional view of the therapy machine of FIG. 1 taken along line 2—2 of FIG. 1 showing the lateral orientation of the treatment and imaging sources.

Referring also to FIG. 2, the bore 13 includes internal recesses 16, 19 and 16', each generally cylindrical and co-axial with the bore axis 15. Recess 16 is disposed near the front surface 24 of the protective barrier 12 and receives the radially outer edge of an annular ball bearing 27 as will be described below. Recess 16' is similar to recess 16 but displaced along the axis of the bore 13 near the back surface 25 of the protective barrier 12. Recess 16' holds the radial outer edge of annular ball bearing 27'.

Centered between recesses 16 and 16' is recess 19 having a radius greater than recess 16 or 16' so as to form a volume for the support of various equipment, to be described, outside of the volume of the bore 13.

Figure 2A:
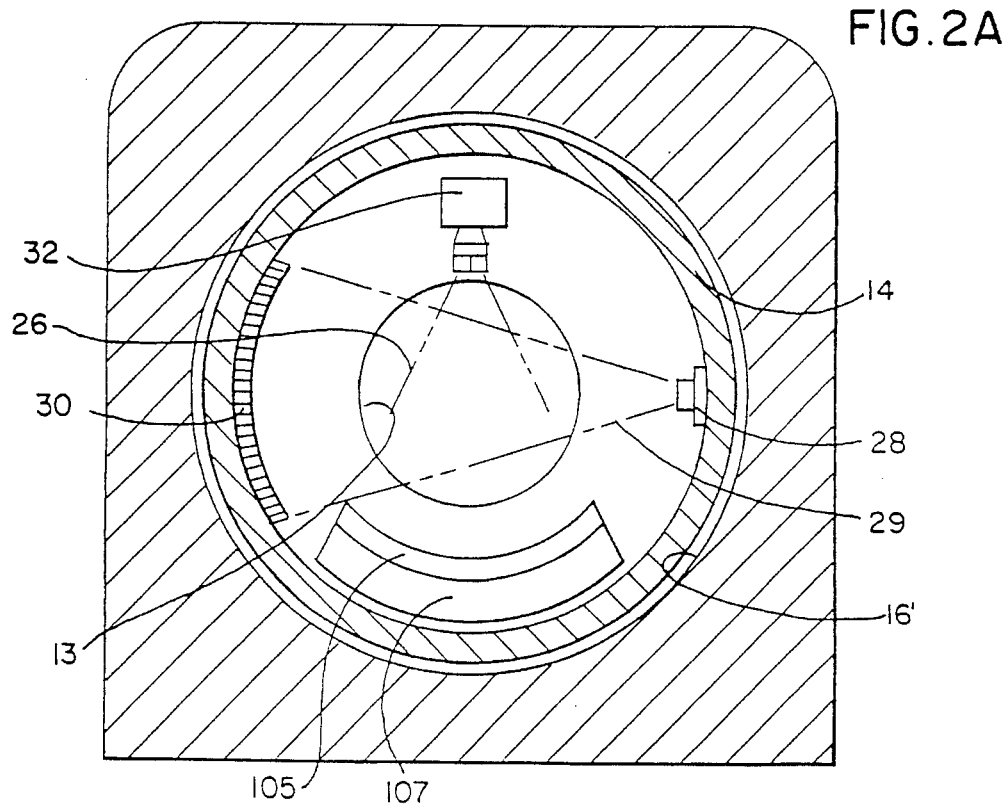
FIG. 2(a) is a cross sectional view of the therapy machine of FIG. 1 taken along line 2A—2A of FIG. 2 showing the radial orientation of the treatment and imaging sources as well as the detector array.

Referring to FIGS. 2 and 2a, an annular gantry 14, radially symmetric about the bore axis 15, fits within the recesses 16, 16' and 19 and has outer surfaces conforming generally to the recesses 16, 16' and 19'. The gantry 14 is supported at two ends by the radially inner edges of bearings 27 and 27' for rotation on those bearings within the barrier 12. The gantry 14 is generally concave inwardly, having a U-shaped portion 20 held with recess 19' with radially inwardly extending walls 21. Attached to the radially extending wall 21 nearest to the back edge 25 is a radiation therapy source 32 producing a fan beam of high energy radiation 26 directed toward and perpendicular to bore axis 15. The fan beam 15 lies generally within a plane 22 perpendicular to the bore axis 15 and at all times is directed toward the barrier 12.

Diametrically opposed to the therapy source 32 on the opposite side of the gantry 14 is a primary barrier 107. The primary barrier 107 subtends and occludes each ray 47 exiting the patient and hence minimizes scatter within a therapy area. For verification purposes, a megavoltage detector array 105 may be placed on the internal surface of the primary barrier 107.

An x-ray source 28 and an imaging detector array 30 are securely disposed along the vertically extending walls 21 closest to the front end 24 of the barrier 9 so as to direct a beam of x-rays 29 along a plane parallel to, but spaced from plane 22 and along an axis at substantially right angles to that of the fan beam 26. This spacing of the plane of the x-rays 29 and fan beam plane 22 ensures sufficient space within the barrier 9 to house the therapy source 32 and x-ray source 28 and prevents unwanted signal interference between the two systems.

The radiation source 32, primary barrier 107, the x-ray source 28 and x-ray detector 30 are all removed from the volume of the bore 13 so as not to interfere with a patient within the bore 13 upon rotation of the gantry 20.

The gantry 20 may be rotated by a shaft 7 extending through the barrier 12 and driven by conventional means. Attached to the shaft is an encoder (not shown) for providing signals indicating the exact angle of the gantry 20 within the barrier 12.

I. The Compensator and Collimator

Figure 3:
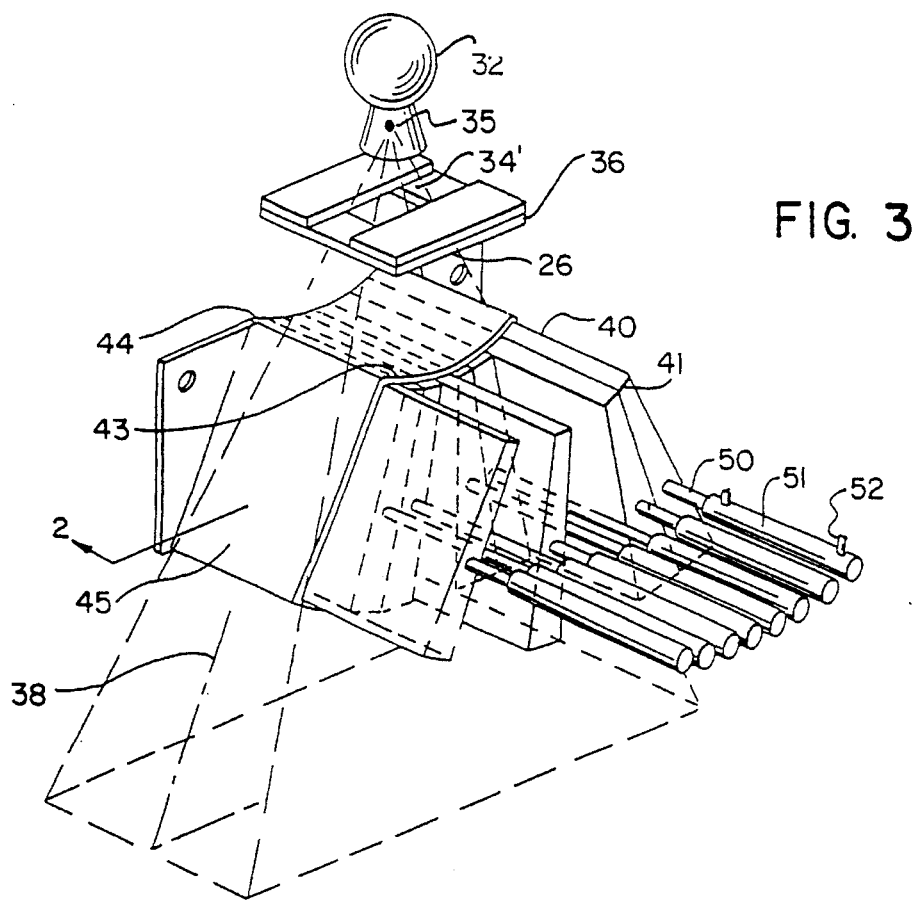
FIG. 3 is a perspective view of the compensator assembly used in the present invention, showing the compensator leaves and their associated motive sources (e.g. pneumatic cylinders)

Referring now to FIG. 3, a radiation therapy source 32 produces a generally conical radiation beam 34' emanating from a focal spot 35 and directed towards a patient (not shown). The conical beam 34 is collimated by a radiational opaque mask 36 constructed of a set of rectangular collimator blades to form a generally planer fan beam 26 centered about a fan beam plane 38.

A compensator 40 is centered in the fan beam 26 produced by the therapy source and about the fan beam plane 38, prior to the radiation being received by the patient, and includes a plurality of adjacent trapezoidal leaves 41 which together form an arc of constant radius about the focal spot 35. The leaves 41 are held in sleeves 43. The sleeves 43 are constructed of relatively radio translucent materials and attached at their inner ends 44 to a mounting plate 45 which is fixed relative to the focal spot 35. The mounting plate 45 is constructed of a sturdy, radiopaque material and is positioned just outside the fan beam 26 to prevent interference with the fan beam 26.

Figure 4:
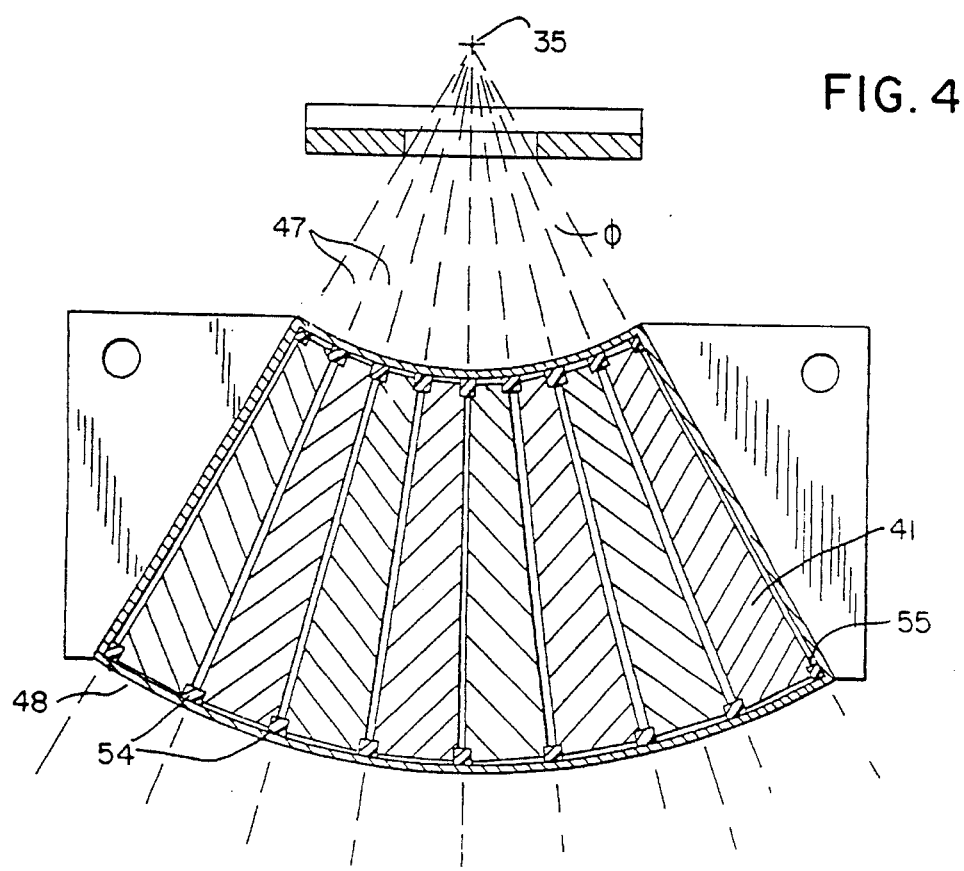
FIG. 4 is a cross-section of the compensator assembly of FIG. 3 along line 4—4 showing the trapezoidal aspect of each compensator leaf, for a fan beam of radiation, and the guide rails for supporting the compensator leaves when they move.

Preferably, the leaves 41 of the compensator 40 subtend the entire fan beam 26 to divide the fan beam 26 into a set of adjacent slab-like rays 47 at offset angles φ. Referring also to FIG. 4, each sleeve 43 is open at its outer end 48 to receive, by sliding, a comparably sized trapezoidal leaf 41 constructed of a dense, radiopaque material such as lead, tungsten, cerium, tantalum or a related alloys.

Each leaf 41 may slide completely within its corresponding sleeve 43 to block the ray 47 associated with that sleeve 43. When the leaf 41 blocks its corresponding ray 47, it is referred to as being in a "closed state". The sleeves 43 are of ample length to permit each leaf 41 to slide out of the path of the fan beam 26, so as to leave its corresponding ray 47 completely unobstructed, and yet to still be guided by the sleeve 43. In this non-blocking position, a leaf is referred to as being in the "open state".

Each leaf 41 may be moved rapidly between its open and closed states by means of a corresponding pneumatic cylinder 51 connected to the leaf 41 by a flexible link 50. The pneumatic cylinders 51 have internal pistons (not shown) that may be moved at high velocity between the ends of the cylinders 51 by means of pressurized air coupled to the cylinders 51 through supply hoses 52. The supply hoses 52 are fed by a compensator control to be described below. The pneumatic cylinders 51 are capable of applying high forces to the leaves 41 to move them rapidly and independently between the open and closed states.

Figure 5:
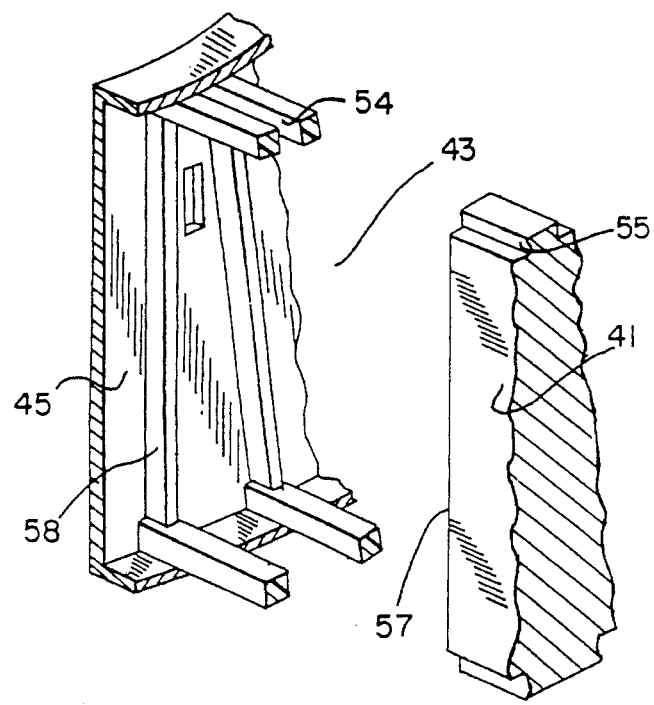
FIG. 5 is a cutaway perspective view of a set of guide rails and one leaf of FIG. 4 showing a collar for supporting the leaf in its fully closed position.

Referring now to FIGS. 4 and 5, the leaves 41 are supported and guided within the sleeves 43 by guide rails 54 fitted into notches 55 cut along the edges of the leaves 41. The notches 55 allow the guide rails 54 to slidably retain the leaves 41 within the sleeves 43 during motion between the open and closed states.

In the closed state, the inner end 57 of each leaf 41 is captured by a rigid collar 58 attached to the mounting plate 45, which aligns the leaf 41, more accurately than may be done by the guide rails 54, with the mounting plate 45 and hence with the fan beam 26. Whereas the guide rails 54, which are ideally radio translucent, are relatively insubstantial, in contrast, the collar 58, positioned outside the fan beam 26 on the mounting plate 45, need not be radiotranslucent and hence is more substantial in construction. A collar (not shown) similar to collar 58, supports each leaf 41 when it is fully in the open state. Because the leaves 41 spend most of their time fully in the open or closed states, they are, at most times, firmly located by a supporting collar.

II. Radiation Therapy Control Circuitry

Figure 6:
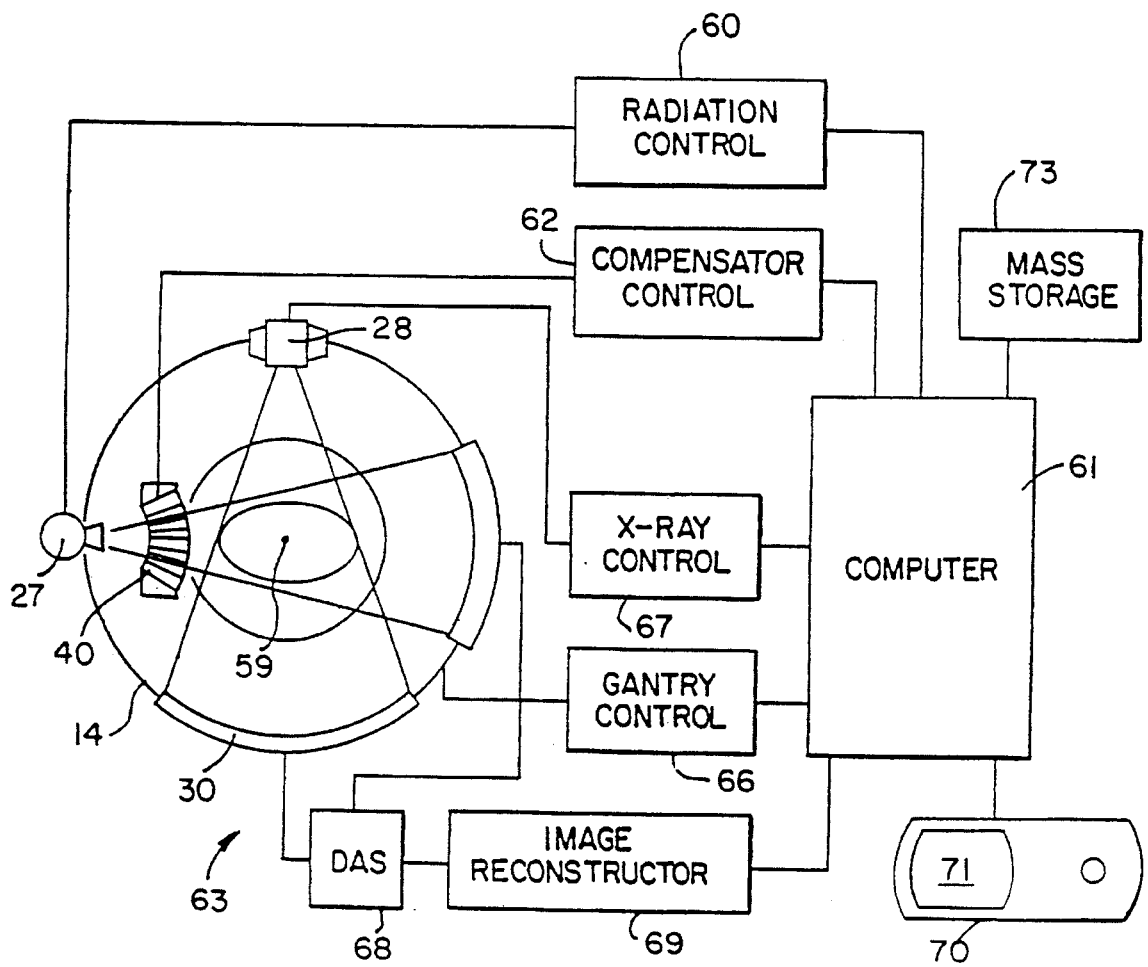
FIG. 6 is a block diagram showing the elements of a radiation therapy apparatus incorporating a conventional CT scanner and the compensator of the present invention and including a computer suitable for controlling that compensator per the present invention.

Referring now to FIG. 6, the radiation therapy source 32 is controlled by a radiation control module 60 which turns the radiation beam 26 on or off under the control of a computer 61.

A compensator control module 62 provides a source of compressed air and valves to gate that air through supply hoses 52 to control, separately, the pneumatic cylinders 51 to move each of the leaves 41 in and out of its corresponding sleeve 43 and ray 47 (see also FIG. 3). The compensator control module 62 also connects with the computer 61 to allow program control of the compensator 40 to be described.

A collimator module 64 controls the spatial relationship between the collimator jaws 156, 157 to effect a single steady state collimated beam 26. The collimator module 64 is also connected to the computer 61 to allow program control of the collimator jaws 156, 157 to be described.

A tomographic imaging system 63 employing the x-ray source 28 and the opposed detector array 30 are advantageously mounted on the same gantry 14 as the radiation source 32 to produce a tomographic or slice image of the irradiated slice of the patient 59 prior to radiation therapy for planning purposes. Control modules for the tomographic imaging system 63 include: x-ray control module 67 for turning on and off the x-ray source 28, and data acquisition system 68 for receiving data from the detector array 30 in order to construct a tomographic image. An image reconstructor 69 typically comprising a high speed array processor or the like receives the data from the data acquisition system 68 in order to assist in "reconstructing" a tomographic image from such data according to methods well known in the art. The image reconstructor 69 also communicates with computer 61 to assist in high speed computations used in the present invention as will be described below. The tomographic image allows verification of the patient setup just prior to radiation therapy treatment.

A gantry control module 66 provides the signals necessary to rotate the gantry 14 and hence to change the position of the radiation source 32 and the angle $\phi$ of the fan beam 26 for the radiation therapy, as well as to change the position of the computed tomography x-ray source 28, the x-ray detector array 30 and the primary barrier 107. Gantry control module 66 connects with computer 61 so that the gantry may be rotated under computer control and also to provide the computer 61 with a signal indicating the gantry angle $\phi$ to assist in that control.

A terminal 70 comprising a keyboard and display unit 71 allows an operator to input programs and data to the computer 61 and to control the radiation therapy and tomographic imaging equipment 63 and to display tomographic images produced by the image reconstructor 69 on the display 71. A mass storage system 73, being either a magnetic disk unit or drive for magnetic tape or optical media, allows the storage of data collected by the tomographic imaging system 11 for later use.

Computer programs for operating the radiation therapy system 10 will generally be stored in mass storage unit 73 and loaded into the internal memory of the computer 61 for rapid processing during use of the system 10.

III. Operation of the Therapy System

As part of a therapy planning session, a patient is placed on the translation table 11 and translated through the gantry 14. During translation the x-ray imaging source 28 is rotated about the patient while directing an x-ray beam 29 toward the detector array 30. Through detecting methods well known in the art, the x-ray source 28 and detector array 30 cooperate to produce x-ray data from a plurality of gantry angles $\phi$ and table positions. The computer 61 stores the raw x-ray data. This data is used by the reconstructor 69 to produce tomographic images of each slice of the patient that are in turn used to generate treatment sinograms for therapy sessions.

Each sinogram contains a plurality of fluence profiles that will control the compensator during a later therapy session. The fluence profiles describe the intensity or fluence of each ray 47 of the radiation beam 26 from the radiation source 32 that is desired for that gantry angle $\phi$ at a given position of the patient translation table (not shown) as translated through the radiation beam 26. Together, the fluence profiles for each gantry angle make up a treatment sinogram for a particular position of the translation table 11.

During operation of the radiation therapy unit 10, the compensator control module 62 receives from the computer 61 a fluence profile for each gantry angle. The compensator control module 62 moves the leaves 41 of the compensator 40 rapidly between their open and closed states to either fully attenuate or provides no attenuation to each ray 47. Gradations in the fluence of each ray 47, as needed for each fluence profile, are obtained by adjusting the relative duration during which each leaf 41 is in the closed position compared to the relative duration during which each leaf 41 is in the open position, for each gantry angle. The ratio between the closed and open states or the "duty cycle" for each leaf 41 affects the total energy passed by a given leaf 41 at each gantry angle and thus can generate arbitrarily shaped beam fluence profiles. The ability to control the beam fluence profile at each gantry angle permits accurate control of the dose provided by the radiation beam 26 through the irradiated volume of the patient 59 by therapy planning methods to be described below.

The fluence profiles of the treatment sinogram are determined by therapy planning software (described below) and stored in the computer 61.

IV. Therapy Planning Software

Figure 7A:
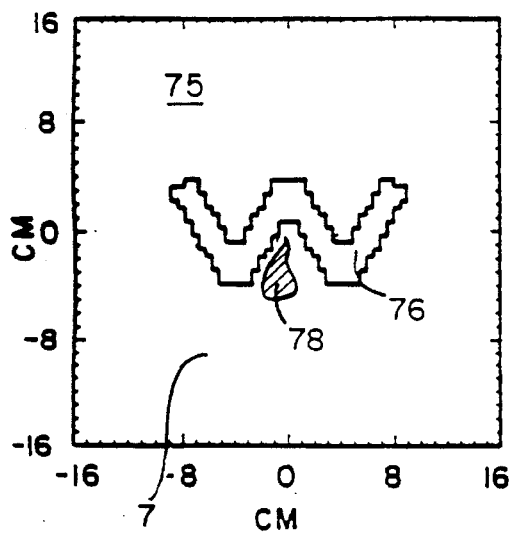
FIGS. 7(a)–(d) are dose distributions of a hypothetical tumorous region showing dose intensity by lines of equal dose, with FIG. 7 (a) showing a desired dose distribution and FIGS. 7 (b), (c), and (d) showing progressive actual dose distributions after two, three and ten iterations per present invention.

Referring to FIG. 7(a), after tomographic images corresponding to various slices of the tumor are generated by the reconstructor 69, the generation of the desired treatment sinogram to control compensator 40 begins with the definition of a desired dose map 75. The desired dose map 75 may be most easily entered by displaying the tomographic image of each slice of a patient on the display 71 of the terminal 70 and manually tracing around the tumorous area 76 using a track-ball or similar input device as is well understood in the art. Standard area-filling computer programs may be used to transfer the dose values assigned to each traced region to the appropriate element in the array of memory representing the desired dose map 75.

A typical desired dose map 75 assigns a relatively high radiation dose, within a dose constraint, to an area of tumorous tissue 76 and a second lower radiation dose to the area of healthy tissue 77 outside of that region.

The healthy tissue 77 may include an area 78 including a radiation sensitive organ or the like to which an even lower radiation dose may be assigned. The desired dose map 75 is stored within the memory of computer 61 as an array of elements each element holding one digital value.

Each element of the dose map 75 thus defines the dose desired at each of the plurality of volume elements 80

Figure 8:
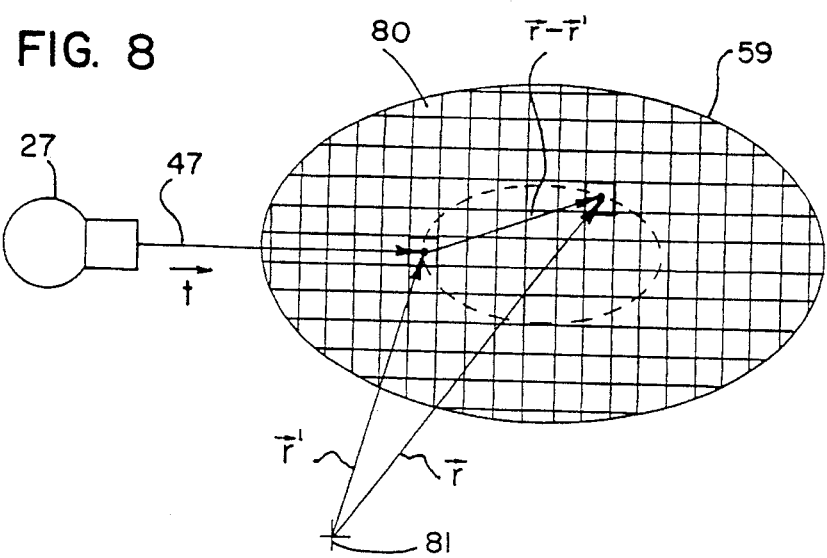
FIG. 8 is a diagrammatic representation of a patient receiving radiation therapy, showing the scatter kernel and the coordinate system used to describe the present invention.

("voxels") within a slice of the patient 59. Referring to FIG. 8, each voxel 80 of the patient 59 may be identified by a vector $\vec{r}$ defined from a given reference point 81. The dose at each voxel 80 is $D(\vec{r})$.

A. Converting Dose to Terma

1. Terma

Generally, the dose at any voxel $\vec{r}$ will depend on the energy received at that voxel $\vec{r}$ from radiation scattered from adjacent voxels $\vec{r}'$ (where adjacent voxels $\vec{r}'$ include the voxel $\vec{r}$, i.e., the radiation received directly from the radiation source 32). The dose $D(\vec{r})$ for a given voxel $\vec{r}$ is given by the following formula:

$$D(\vec{r}) = \int T(\vec{r}')A(\vec{r}-\vec{r}')d^3\vec{r}' \qquad (1)$$

where $T(\vec{r}')$ is a value indicating the magnitude of the primary total energy released from $\vec{r}'$ per unit mass of that voxel $\vec{r}'$ and is called the "terma" (total energy released per unit mass).

For a monoenergetic external radiation source, the terma rate $\dot{T}(\vec{r})$ is described by:

$$\dot{T}(\vec{r}) = \frac{\mu}{\rho}(\vec{r})E\int\phi(\vec{r})dt \qquad (2)$$

where $\mu/\rho$ is an effective mass attenuation value at the voxel $\vec{r}$, E is the energy of the radiation photons in Joules, $\phi$ is the distribution of the fluence rate (flux density). The integration of energy times fluence rate over time is energy fluence $\Psi(\vec{r}')$ where:

$$\Psi(\vec{r}') = E\int\phi(\vec{r}')dt \qquad (3)$$

hence $$T(\vec{r}) = \frac{\mu}{\rho}(\vec{r})\Psi(\vec{r}) \qquad (4)$$

Equation (4) basically relates how much energy from the ray 47 interacts with the voxel r'.

2. Convolution Kernel $A(\vec{r}-\vec{r}')$ is a convolution kernel describing non-stochastic energy transport or scattering in a uniform medium. $A(\vec{r}-\vec{r}')$ thus describes how the energy from each voxel $\vec{r}'$ spreads to contribute to the dose at voxel $\vec{r}$.

The kernel $A(\vec{r}-\vec{r}')$ may be generated using a Monte Carlo method as is generally understood in the art. As mentioned, it is a three-dimensional function indicating the fraction of energy absorbed at voxel $\vec{r}$ per unit of energy released at voxel $\vec{r}'$. The energy emitted from the terma of each voxel $\vec{r}'$ finds it source in a directed ray 47 from external radiation source 32 and thus $A(\vec{r}-\vec{r}')$ is generally anisotropic as suggested in FIG. 9, spreading outward away from the entry of ray 47. Energy conservation requires that:

$$\int A(\vec{r}')d^3\vec{r}' = 1.0 \qquad (5)$$

That is, if the energy transferred by the primary interaction were all deposited on the interaction point, the kernel would be approximated as a delta function.

Figure 9:
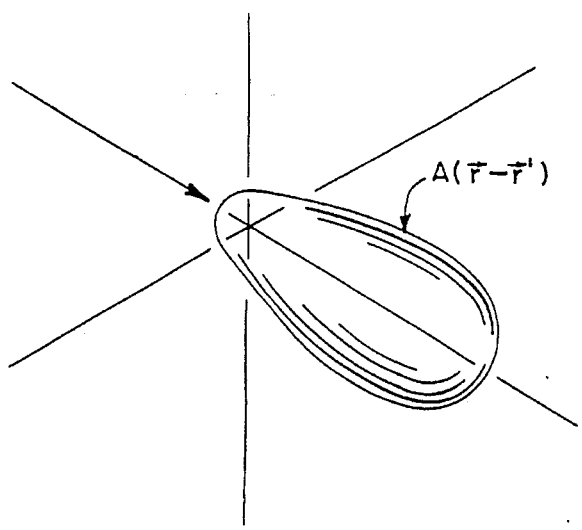
FIG. 9 is a perspective representation of a monodirectional scatter kernel associated with a radiation beam at one gantry angle.

Referring still to FIG. 9, the anisotropy of $A(\vec{r}-\vec{r}')$ is related to the gantry angle $\phi$ and thus of the angle of incidence of the ray 47 at $\vec{r}'$. If the gantry angles $\phi$ at which the patient 59 is irradiated are predetermined, a multidirection convolution kernel $B(\vec{r}-\vec{r}')$, shown in FIG. 10, may be created from weighted superimposition of the kernels $A(\vec{r}-\vec{r}')$.

Figure 10:
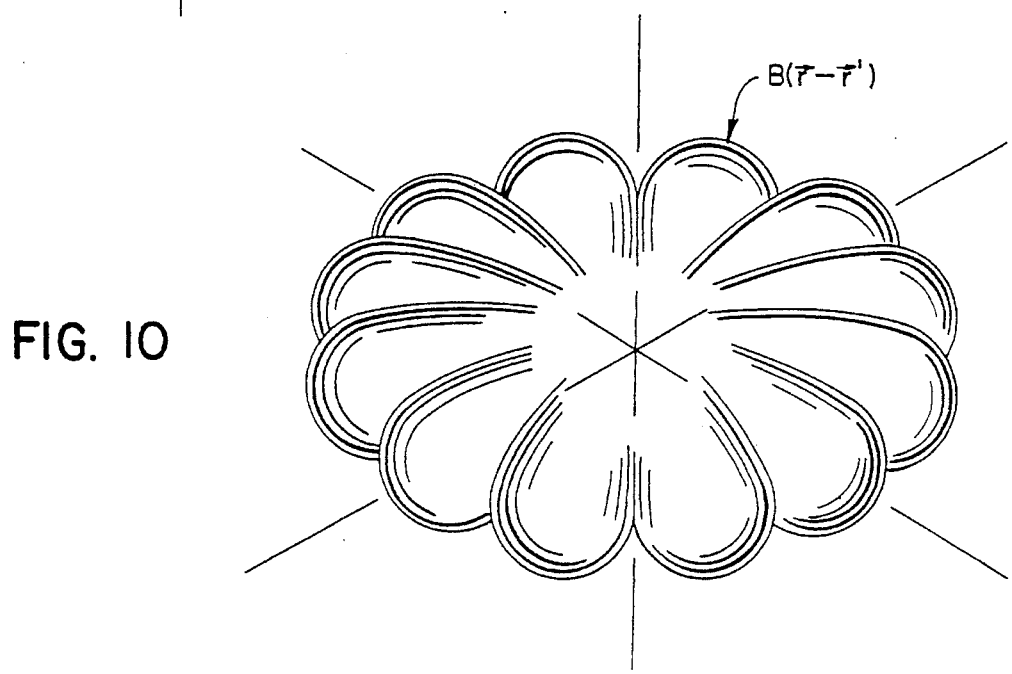
FIG. 10 is a perspective representation of a composite multidirectional scatter kernel associated with a plurality of radiation beams at multiple gantry angles.

Referring to FIG. 10, assuming that the spreading of radiation is approximately equal for all beam directions and the rays 47 from each gantry angle $\phi$ contribute equally to the terma at voxel $\vec{r}'$, then the multidirectional convolution kernel reduces to a "isotropic" form as follows:

$$B(\vec{r}-\vec{r}') = \frac{1}{n}\sum_{i=1}^{n}A(\vec{r}-\vec{r}')_i \qquad (6)$$

where n is the number of discrete gantry angles from which rays 47 are projected.

For multiple rays 47 at different gantry angles, the total dose at a given voxel $\vec{r}$ is the sum of doses from each constituent beam is therefore:

$$D(\vec{r}) = \int T(\vec{r}')B(\vec{r}-\vec{r}')d^3\vec{r}' \qquad (7)$$

where $T(\vec{r}') = nT(\vec{r}')_i$, the latter term being the contributed portion of the terma for the ith gantry angle.

This simplification assumes that the contribution to the terma from each ray 47 is equivalent and takes advantage of the distributive property of convolution. Errors in this assumption are reduced by the filtration to be discussed later.

Equation (7) substantially simplifies the calculation of dose from terma but still requires a convolution for each voxel $\vec{r}$ times the total number of voxels $\vec{r}'$ to calculate the dose over the entire patient volume. Preferably, therefore, the calculational efficiency of the fast Fourier transform can be used and equation (7) converted to the following:

$$D(\vec{r}) = F^{-1}\{F\{T(\vec{r}')\}\cdot F\{B(\vec{r}-\vec{r}')\}\} \qquad (8)$$

where F and $F^{-1}$ symbolize Fourier and inverse Fourier transforms respectively. This simplification of equation (8) requires that the kernel $B(\vec{r}-\vec{r}')$ be spatially invariant and relies on the convolution theorem which states that convolution of two spatially invariant quantities in a space domain is equivalent to multiplication in the frequency domain.

The assumption of the spatial invariance of $B(\vec{r}-\vec{r}')$ is correct only to a first order approximation. Typically, the kernel $B(\vec{r}-\vec{r}')$ for an external radiation source 32 is a complex function of: (1) beam hardening of a polyenergetic x-ray beam (i.e., the effect of the filtration of the patient 59 in increasing the proportion of high frequency or high energy radiation components), (2) the number of rays 47 crossing each voxel, and (3) exponential attenuation by the patient mass.

In the preferred embodiment, this first factor, beam hardening, is neglected because it is an effect smaller than the attenuation problem. Thus, the photon energy spectrum in the patient 59 may be assumed to be the same as that of the external radiation source 32. This simplification is not required, however, and it will be understood that beam hardening could be accurately accounted for by representing a photon energy spectrum by a finite number of separately convolved energy intervals.

The second factor, the difference in the number and orientation of rays 47 that cross each voxel, caused by the geometry of a finite number of gantry angles and the fan orientation of the beam 26, affect spatial invariance. Problems arising from the fan orientation of the beam (in contrast to a parallel beam geometry) are largely solved if there is a full rotation of the gantry 14. Errors resulting from the fact that irradiation is performed at only a finite number of gantry angles have been determined to be acceptable.

The third factor affecting the assumption of spatial invariance is the attenuation of the medium. This affects the fractional contribution of the total terma from the beams at each gantry angle. Accordingly, in those steps of the planning procedure, as will be noted below, where accurate calculation of dose is critical, the dose distribution is calculated separately for each beam based on the attenuation of overlying voxels, such attenuation deduced from the parameters of the tomographic image. In this case the simplification of equation (8) may not be employed and repeated convolutions must be performed. In certain steps in the planning process, however, as will be noted, an estimate is sufficient and in these cases $B(\vec{r}-\vec{r}')$ is assumed to be spatially invariant and the dose calculated according to equation (8).

Production of terma values from a desired dose map 75 is then simply the process of inverting equation (8) as follows:

$$T(\vec{r}) = F^{-1}\left\{ \frac{F\{D(\vec{r})\}}{F\{B(\vec{r}-\vec{r}')\}} \right\} \quad (9)$$

This inversion requires that there be no significant "zeros" (typically at high frequencies) in the denominator term $F\{B(\vec{r}-\vec{r}')\}$ or more simply that the kernel $B(\vec{r}-\vec{r}')$ be spatially compact (i.e., the Fourier transform of a spatially compact kernel will have significant high frequency content). It has been determined by the present inventors that the kernels dictated for patients 59 are sufficiently compact to allow this Fourier deconvolution.

Figure 11:
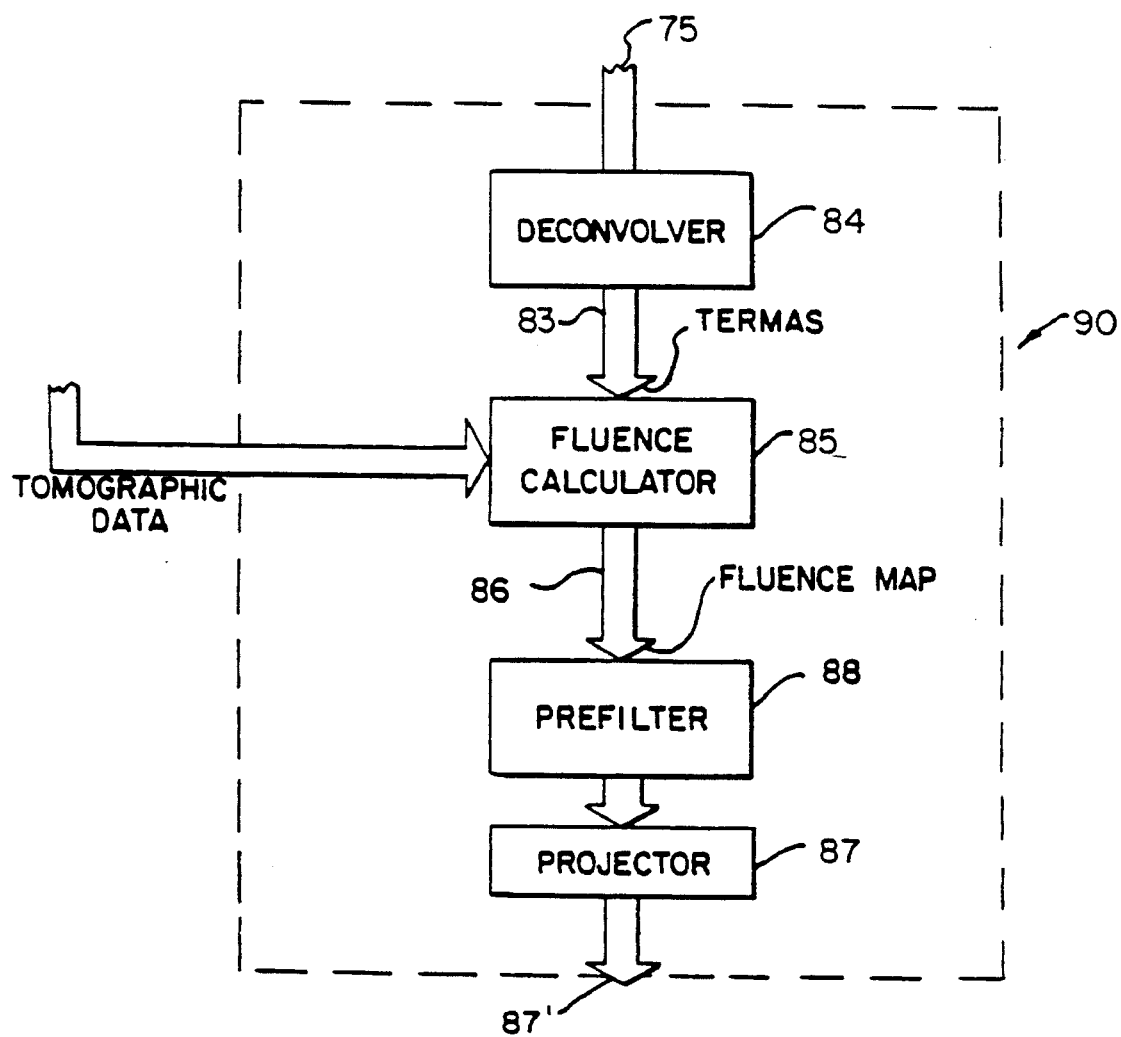
FIG. 11 is a block diagram depicting the fluence profile calculator which takes a desired dose map and calculates a fluence profile.

Referring now to FIG. 11, this deconvolution to produce a terma map 83, giving the terma for each voxel $\vec{r}$, from the desired dose map 75, is represented by process block 84.

B. Converting Terma to Voxel Energy Fluence

Knowing the terma map 83, the energy fluence $\Psi(\vec{r}')$, which is a measure of the beam intensity, can be determined at each corresponding voxel by equation (4) from a knowledge of $\mu/\rho$ as follows:

$$\Psi(\vec{r}) = \frac{T(\vec{r})}{\frac{\mu}{\rho}(\vec{r})} \quad (10)$$

The value of $\mu/\rho$ may be estimated and considered a constant or actual $\mu/\rho$ may be deduced from the tomographic scan data collected by means of the tomographic imaging system 63, (shown in FIG. 6). In this manner and as illustrated by process block 85 of FIG. 11, a fluence map 86 giving the fluence at each point of the terma map may be determined.

C. Converting Voxel Energy Fluence to Energy Fluence Profile

The energy fluence $\Psi(\vec{r}')$ at each voxel $\vec{r}'$ is related to the energy of the ray 47 exiting the compensator 40 by the relation:

$$\Psi(\vec{r}') = \Psi_0(\phi,\theta)\, e^{-\int \mu/\rho(\vec{r})\rho(\vec{r})\delta(p-\hat{r}\cdot\vec{r})dt}\left(\frac{SSD^2(\phi,\theta)}{|\vec{r}|^2}\right) \quad (11)$$

where $\Psi_0(\phi,\theta)$ is the energy fluence for a given ray 47 as described by $\delta(p-\hat{r}\cdot\vec{r})$ at the exit of the compensator 40 and serves to define the fluence profile of the compensator and $\theta$ and $\phi$ are the gantry angle and the offset angles of the ray 47 as previously described.

The exponential term represents the attenuation of the ray 47 from the exit of the compensator 40 to the voxel $\vec{r}$ caused by the mass of the patient 59 where by $\mu/\rho(\vec{r})$ is the attenuation for each voxel $\vec{r}$ along the ray 47, $\rho(\vec{r})$ is the density of each voxel $\vec{r}$, SSD $(\phi,\theta)$ is the distance between the exit of the compensator 40 and the surface of the patient 59, $\hat{r}$ is a unit vector along $\vec{r}$ (where the origin of is now assumed to be the center of rotation of the gantry 14), and p is the perpendicular distance from the gantry's center of rotation 15 and the ray 47. The vector is simply a vector along the ray 47 to provide an integration variable.

The fluence at each voxel $\vec{r}$ is related to the fluence of the radiation beam 26 emitted from the compensator 40 by equation (11). In the preferred embodiment, the density and attenuation of each voxel $\vec{r}$, $\mu/\rho(\vec{r})$ and $\rho(\vec{r})$ are assumed to be constant and the fan beam of radiation is approximated by a parallel beam, hence $$\frac{SSD^2(\phi,\theta)}{|\vec{r}|^2} = 1$$

Borrowing from the mathematics of tomographic image reconstruction, the fluence map 86 may be "reverse" back projected (i.e. projected) by projector 87 to determine a fluence profile to be produced by the external-source necessary to generate the desired fluence map and hence dose.

This projection is simply the opposite of a typical back projection used to form an image of a tomographic slice of a patient 59 from a series of projections taken in a tomographic imaging system. Because a projection is a line integral across a distribution, the energy fluence distribution for each voxel (equation (11)) is first differentiated with respect to the rayline $\vec{t}$:

$$\frac{d\Psi(\vec{r})}{dt} = \left[\frac{\mu}{\rho}(\vec{r})\rho(\vec{r})\delta(p-\hat{r}\cdot\vec{r}) + \frac{2}{t}\right]\Psi(\vec{r}) \quad (12)$$

The line integral of $$\frac{d\Psi(\vec{r})}{dt}$$

along $\vec{t}$, corrected for attenuation and inverse-square fall off, then represents the projection operation and $\Psi_0(\phi,\theta)$, the fluence profile over the offset angles $\phi$ of each gantry angle $\theta$, is:

$$\Psi_0(\phi,\theta) = \int \left[ \frac{\mu}{\rho} (\vec{r})\rho(\vec{r})\delta(\rho - \hat{r}\cdot\vec{r}) + \frac{2}{t} \right] \times \quad (13)$$

$$(\psi(\vec{r})e + \int \mu/\rho(\vec{r})\rho(\vec{r})\delta(\rho - \hat{r}\cdot\vec{r})d\vec{t}\left( \frac{|\vec{r}|^2}{SSD^2(\phi,\theta)} \right) \times (p - \hat{r}\cdot\vec{r})d\vec{t}$$

The projection of equation (13) is represented by projector 87 in FIG. 11.

The projection process, for the purpose of computing fluence profiles for the compensator 40, differs in a fundamental way from the simple inverse of tomographic back projection. The difference is primarily in a concern for the sharpness in the transition of the dose between the irradiated tumorous tissue 76 and the healthy tissue 77. Sharpness in this transition region reduces the irradiation of healthy tissue 77 and is preferred over actual fidelity of the dose to the desired dose map 75.

For this reason, the fluence map 86 from the fluence calculator 85 is prefiltered as shown by process block 88 to produce a filtered fluence map $\Psi'(\phi,\theta)$ as follows:

$$\Psi'(\phi,\theta) = F^{-1}\{F\{\Psi(\phi,\theta)|\omega|\}_{30} \quad (14)$$

where $\Psi(\phi,\theta)$ is the fluence map 86 and $|\omega|$ is a ramp filter in frequency space and the '+' subscript indicates the positive component of the filtering result. This prefilter 88 serves to increase the high frequency content of the fluence map 86 and thus to aid in rapid transition of dose at the tumor/non-tumor interface.

It is noted that this prefilter 88 is similar to the filter used in tomographic imaging's "filtered" back projection. That is, like tomographic imaging, the filter de-emphasizes the low frequency components of the projection in producing image data. In addition other prefilters may be applied to correct for the use of the radially symmetric kernel (equation (6)) in computing the dose map from the terma map composed from the fluence profile In practice the computation of a terma map, the generation of a fluence map and the calculation of the fluence profiles need not be performed as discrete steps but may be accomplished by a direct projection of the dose map with appropriate filtering. The filtering is accomplished by a "fast inversion filter" which combines in projection space the operation of deconvolution and ramp filtration.

This may be symbolically specified by the following equation $$\Psi(\phi,\theta) = \rho\{D(\vec{r})\} \otimes I(t) \quad (15)$$

where $\rho$ refers to a projection operation and $I(t)$ is the fast inversion filter. The $\otimes$ operators refers to a convolution operation such as would normally be done in Fourier space using a fast Fourier transformation.

Figure 12:
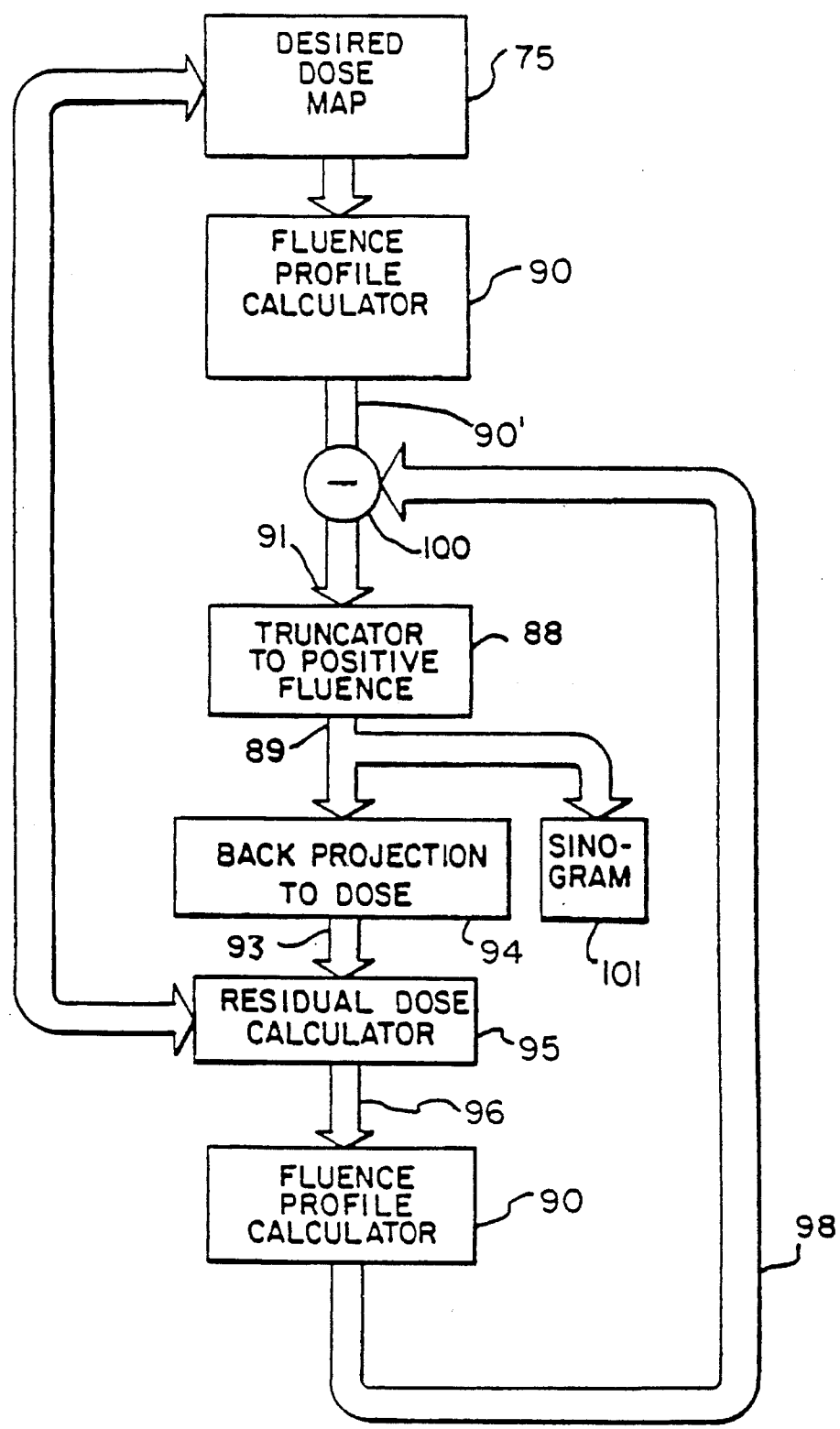
FIG. 12 is a block diagram depicting the overall iterative method of controlling the compensator of the present invention, employing the fluence profile calculation method of FIG. 11.

Referring still to FIG. 12, the fluence profile calculations of block 90, including the deconvolver 84, the fluence calculator 85, the prefilter 88 which includes any projection space filter (such as a ramp filter, a fast inversion filter followed by truncation of zeros), and the projector 87 thus produce fluence profiles which together create an estimated treatment sinogram 91' from the desired dose map 75. The fluence profile calculator 90 may use the Fourier convolution of equation (9) in the estimate of the fluence profiles at this stage, accepting minor inaccuracies in that process, to be corrected at a later stage, as will be described below.

D. Iteration

Referring now to FIG. 14, the fluence profile calculator 90 converts the desired dose map 75 to an estimated treatment sinogram 90', however the fluence profiles of this estimated treatment sinogram 90' may not be used to control the compensator 40 because, in general, the estimated treatment sinogram 90' will include positive and negative values of fluence. Only positive values of fluence are physically realizable by the compensator 40; a negative value of fluence would represent a ray 47 that absorbed radiation along its path which is physically unrealizable.

Accordingly, at process block 88, the fluence values of the estimated treatment sinogram 90' are truncated to positive fluence values 89. As a result of this truncation, the estimated treatment sinogram 90' no longer produces the desired dose map.

The amount of error resulting from the truncation producing the positive fluence profiles 89 is determined by back projecting the positive fluence values 89 to an actual dose map 93 deviating from the desired dose map 75. This back projection is accomplished by computing a fluence map from the positive fluence values 89 per equation (11) and a terma map per equation (4) and then convolving the terma map with the kernel per equation (7) to establish the actual dose map 93 per process block 94 of FIG. 11.

In this back projection, the assumption of spatial invariance of the convolution kernel $B(\vec{r}-\vec{r}')$ is not made so as to produce a more accurate actual dose map 93.

The projection of a fluence profile onto a patient 59 to compute a dose map may be performed by a number of other procedures known to those of ordinary skill in the art.

The actual dose map 93 is compared to the desired dose map 75 to produce residual dose map 96 as indicated by process block 95. In the preferred embodiment, the comparison subtracts from the values of each voxel $\vec{r}$ of the actual dose map 93, the greater of: a) the corresponding value of desired dose map 75, or b) a predetermined upper dose constraint. The predetermined upper dose constraint is a threshold number that is deemed an acceptable dose to tumorous tissue 76. Clearly, other methods of quantifying the difference between the desired dose map and the actual dose map will be apparent from this description to those of ordinary skill in the art.

Figure 13A:
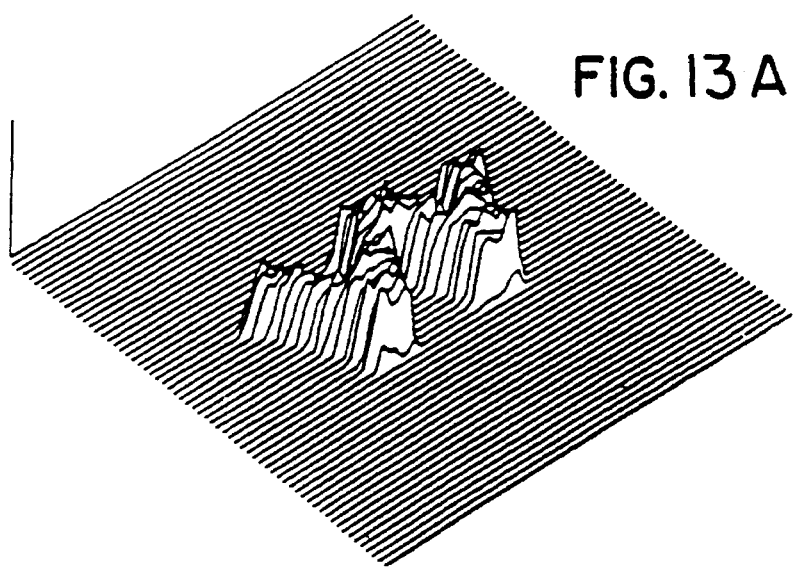
FIGS. 13(a)–(c) are perspective views of plots showing the error between the desired dose distribution and the actual dose distribution obtained with the present invention for one, two and four steps of iteration respectively.

The result of this comparison process 95 is to produce a residual dose map 96 shown in FIG. 13(a). This residual dose map 96 is then, again, operated on by the fluence profile calculator 90 (in lieu of the desired dose map 75) to produce an error fluence profile 98 (in lieu of the estimated treatment sinogram 91).

A thus produced error fluence profile 98 is subtracted by subtracter 100 from the estimated treatment sinogram 90' to produce a new estimated treatment sinogram 90.

Figure 13B:
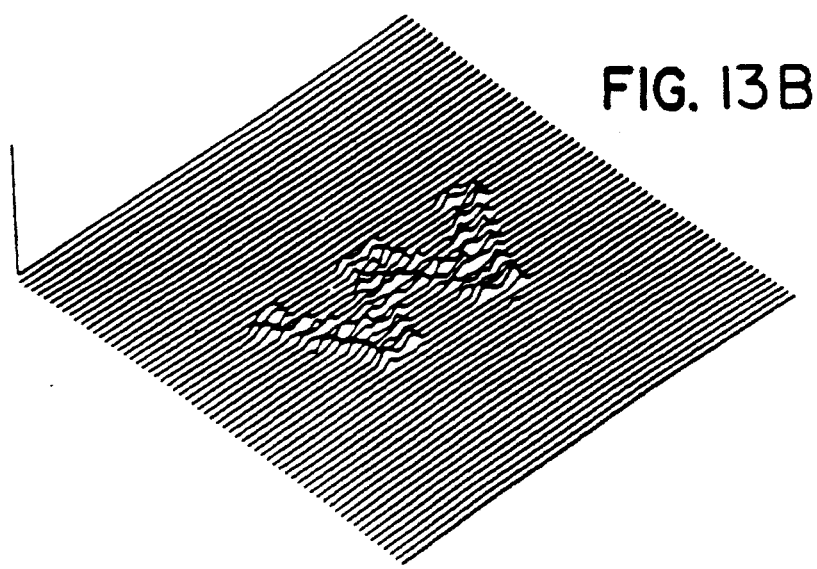
Figure 13C:
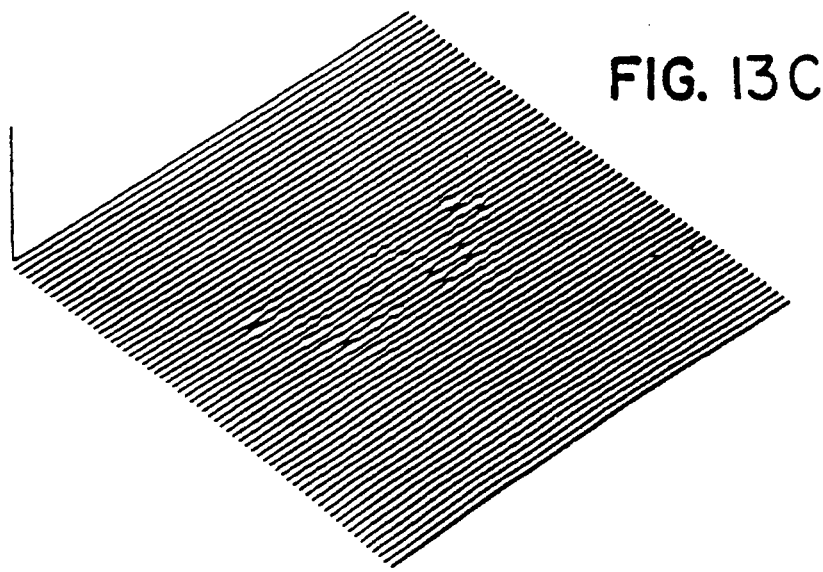

As shown in FIG. 12, this new estimated treatment sinogram 90 is repeatedly operated on by process blocks 88, 94, 95 and 96 for a predetermined number of iterations, the magnitude of the error fluence profile 98 values decreasing with each iteration as shown in FIGS. 13(b)–(c) until a suitably low error fluence profile 98 is obtained.

The the new estimated fluence profile 90 is then truncated per process block 88 to produce a final sinogram 101 for use in controlling the compensator 40 as previously described.

Figure 7B:
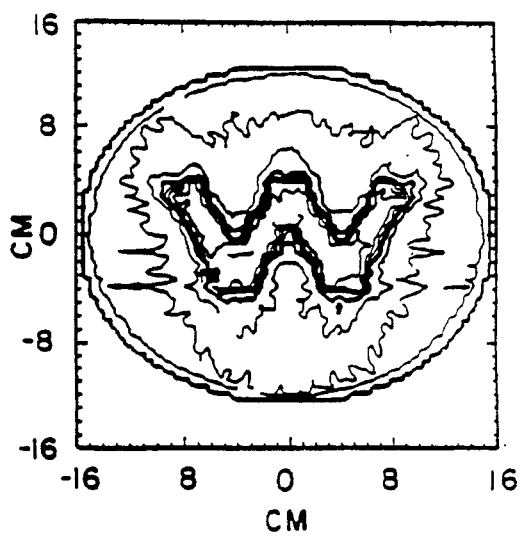
Figure 7C:
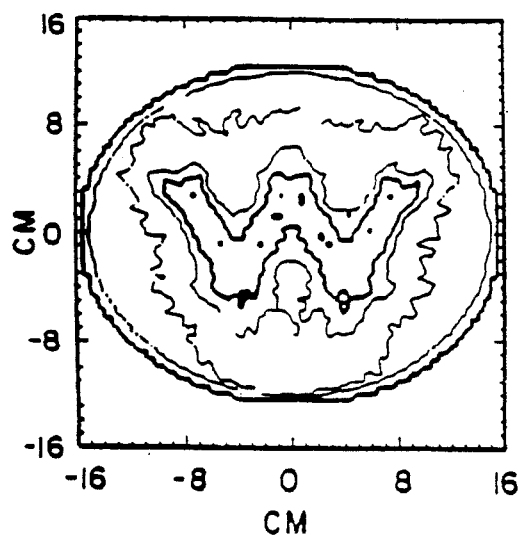
Figure 7D:
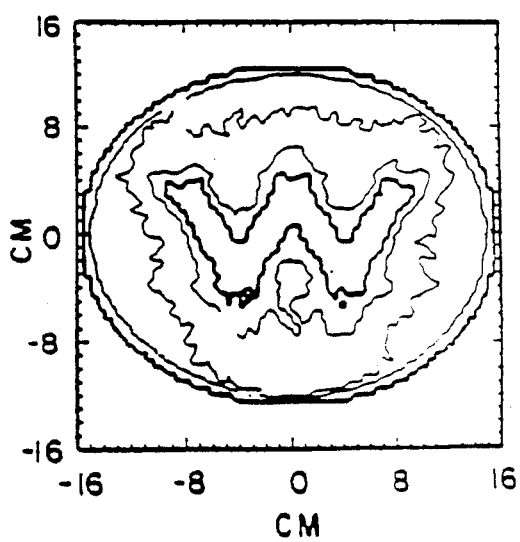

Referring again to Figs.7 (b), (c) and (d), dose maps obtained by the present invention corresponding to a desired dose map 75 of FIG. 7(a) are shown after: one iteration (FIG. 7(b)); two iterations (FIG. 7(c)); and ten iterations (FIG. 7(d)). The variations in dose in the target volume shown in FIG. 7(d) are plus or minus 2% about the predetermined upper limit of 1,000 cGy.

V Helical Scanning

The radiation therapy machine of the present invention, in which the angles of the radiation beams are constrained to a single gantry plane 14, may irradiate adjacent slices of a tumor separately along the translation axis 17 by rotating 360 degrees and then stopping the irradiation and advancing the patient and table by one slice thickness. The next slice can then be treated with 360 degrees of gantry rotation. This type of therapy will be termed "stop and shoot" rotation therapy and allows simple relating of the data generated by the tomographic imaging system 63 and the data used by the radiation therapy machine 10.

It is difficult to use stop and shoot therapy to achieve uniform radiation doses throughout a tumorous volume without "gaps" or "hot" spot. The reason for this is the fact that the fan beam itself is not uniform in cross section. Also, it is difficult to accurately direct the radiation beam along the edges of the adjacent slices.

Figure 14A:
FIG. 14 (a)–(c) are a perspective view of a simplified tumor and graphs showing gaps or hot spots that may result from two junctioned radiotherapy beams.
Figure 14B:
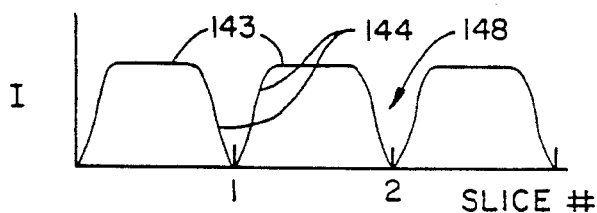
Figure 14C:
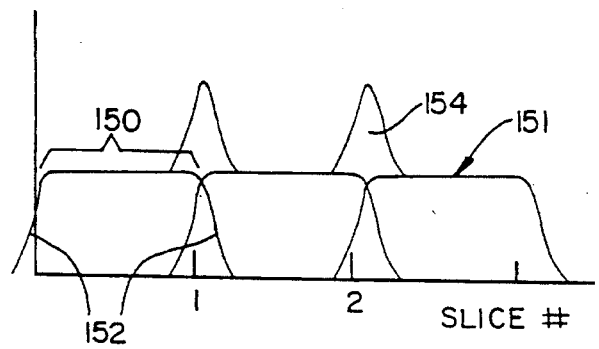

Refer to FIG. 14(b)–(c) fluence profiles 143, 151 of the radiation source 32 are non-uniform, dropping off near the edges 144 of the area exposed by fan beam 26. This is true even in machines employing beam flattening filters.

Because of fluence drop off, the fluence distribution along the length of the tumor 132 is not completely uniform when stop and shoot rotation therapy is employed.

Referring to FIGS. 1, 14(a) and 14(b), if the patient is advanced by exactly one slice width after each 360 degrees of gantry rotation, gaps will be generated. In this situation, a tumor 132 may be translated partially through the gantry 14 until the fan beam 26 subtends only the first slice 133 of the tumor 132. Starting with the gantry 14 at an arbitrary 0° position, the radiation source 32 is energized to produce and direct the fan beam 26 toward the rotation axis 15 while the radiation source 32 is rotated through an entire 360° rotation. After irradiation of the first slice 133, the patient is again translated through the gantry 14 into a second position where the fan beam 26 subtends only the second slice 134. After a second 360° rotation of the radiation source 32 the patient is translated into a third position. This stop and shoot protocol continues until all the slices of the tumor 132 have been irradiated.

Although the slices detuned by the fan beam abut, as shown in FIG. 14(b), this procedure results in radiation gaps 148 along the length of the tumor 132 where the edges 144 of the fluence profiles 143 drop off. Clearly, gaps 148 in radiation dose limit radiation effectiveness and should be avoided if possible.

Referring to FIGS. 14(a) and 14(c), if the patent is translated by less than the slice thickness after each 360° of gantry rotation, radiation gaps 148 can be eliminated, however, radiation hot spots 154 may result. In this case the thickness of the fan beam 26 used to irradiate a tumor 132 is adjusted so that the main portion 150 of each fluence profile 151 subtends an entire tumor slice while the edges 152 of the profile 151 are on either side of the tumor slice. This thick fan beam technique generates radiation "hot spots" 154 where radiation from the faded edges of one fluence profile 151 add to radiation from adjacent profiles 151 as shown in FIG. 14(c).

By adjusting the overlap of adjacent fluence profiles 151, a compromise can be achieved where the gaps 148 and hot spots 154 are minimized. However, because of the nonlinear fluence drop off near the edges 144 of the fan beams 26 (see FIG. 14(b)), stop and shoot beam overlap cannot entirely "smooth" the radiation dose between two adjacent tumor slices.

Machines that can produce a substantially linear fluence drop off at their fan beam edges would make stop and shoot rotation therapy possible. However, without extremely accurate translation and verification systems that provide information on precise patient position within the gantry 14, such machines would not eliminate irradiation gaps or hot spots where an error in patient positioning occurs.

Preferably, therefore a helical scanning pattern is adopted where instead of 360° of gantry rotation in between movement of the patient along the translation axis to the next slice, the patient is continuously translated during rotation of the gantry so that the axis of radiation describes a helical path through the patient. The pitch of the helix; i.e., the distance the patient traverses along the translation axis 17 for each 360° gantry rotation, may be one slice thickness (the width of the radiation window) so that each slice of the tumor is irradiated from all 360°. Clearly other helical patterns of irradiation could be used. Assuming all beam rays 47 are substantially parallel, each slice may be properly irradiated by a 180° source rotation.

Figure 15:
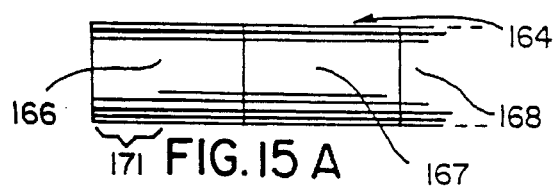
FIG. 15(a) is an elevational view of the simplified tumor of FIG. 14 (a) and FIGS. 15 (b)–(e) are graphs showing the radiation beam position relative to the tumor in FIG. 15 (a) from various gantry angles during a helical therapy session.
Figure 15B:
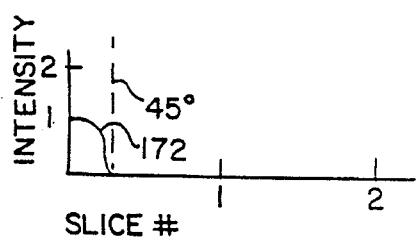
Figure 16A:
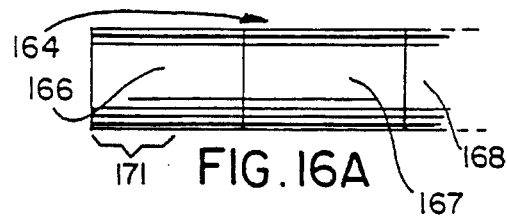
FIG. 16(a)–(e) are an elevational view of the simplified tumor of FIG. 14 (a) and graphs showing the cumulative radiation dose delivered to the tumor in FIG. 16(a) at different times during a helical therapy session, each graph in FIGS. 16(b)–(e) corresponding to an adjacent graph in FIGS. 15 (b)–(e)
Figure 16B:
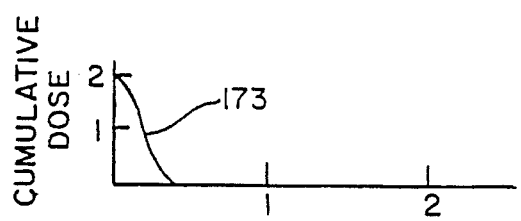
Figure 16C:
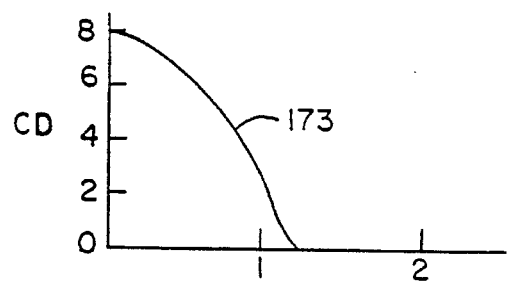

Referring to FIGS. 15(a) and 16(a), a simplified tumor 164 of FIG. 14(a) is divided into similarly sized tumor slices, some being referred to as 166, 167 and 168. Referring to FIGS. 12(a) and 15(b), in helical scanning during the first 45° of gantry rotation, a collimated beam 172 subtends the front part 171 of the first slice 166 and a dose 173 of radiation is absorbed across the front part 171 of the first slice 166. Referring to FIGS. 16(c), as the radiation source 32 rotates from 45° to 180°, one tumor slice is fully exposed and the dose absorbed by the first slice 166 continues to grow.

Figure 15C:
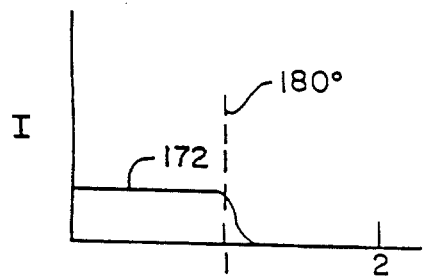
Figure 15D:
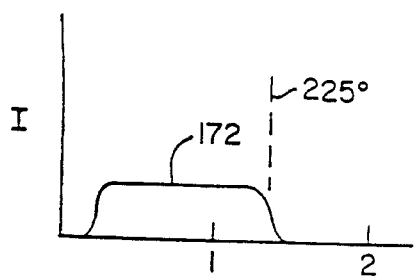
Figure 16D:
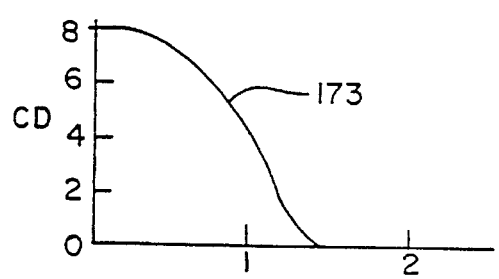

Referring to FIG. 15(d), as the radiation source 32 rotates from 180° to 225° the beam 26 begins to subtend parts of both the first and second slices 166, 167 of the tumor 164. The radiation absorbed by the front portion 171 of the first slice 166 begins to level off (see FIG. 16(d)) as the front part 171 of the tumor 164 moves out of the collimated beam 26.

Figure 16E:
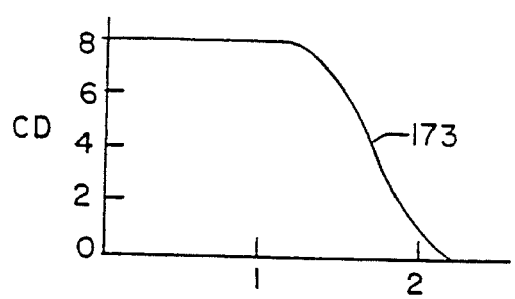

Referring to FIG. 16(e), after a full 360° of rotation, the entire first slice 166 of the tumor 164 has been uniformly irradiated and the gradient absorption is across the second tumor slice 167.

Helical therapy as described above averages the non-uniform fluence profiles 143 of FIG. 14 (b) across and between tumor slice 166, 167 to eliminate hot spots 154 and radiation gaps 148.

V. Generating Helical Data

The fluence profiles used to operate a therapy machine in a helical manner are not identical to those generated in the planning process described previously. Even though the gantry 14 rotates so that the radiation source 32 directs the fan beam 26 at the tumor site from angles identical to those used in developing the final slice sinograms 101, the position of the patient with respect to the fan beam 26 is typically not the same as that used in developing the sinogram because of the helical motion. Accordingly, during a therapy session, when the collimated fan beam 26 subtends parts of different adjacent tumor slices 166, 167 as in FIG. 15(d), the computer 61 must interpolate between the duty cycle of each leaf 41 for the two adjacent slices 166, 167 to produce a duty cycle approximation for the particular gantry angle φ and table position. Again, making the assumption that the rays of the fan beam are substantially parallel a simple weighted averaging calculation using the following equation may be used to generate the duty cycle approximations:

$$\Psi(z_i, z_i+1, \theta_j, \phi_k) = \qquad (16)$$

$$\Psi(z_i, \theta_j, \phi_k)\left(1 - \frac{\rho}{180}\right) + \Psi(z_{i+1}, \theta_j, \phi_k)\left(\frac{\rho}{180}\right)$$

where $z_i$ is the first adjacent slice, $z_{i+1}$ is a second adjacent slice, $\theta_j$ is the gantry angle of the radiation source 32, $\phi_k$ is the compensator leaf angle from the central ray, $\Psi(z_i,\theta_j,\phi_k)$ is the desired fluence of the first tumor slice commonly irradiated (in FIG. 15(a) slice 166), $\Psi(z_{i+1},\theta_j,\phi_k)$ is the fluence of the second tumor slice commonly irradiated (in FIG. 15(a) slice 167), ρ is a second gantry angle, which is 0° when the fan beam 26 first subtends portions of two adjacent slices and ranges from 0° to 180° as the gantry angle $\theta_j$ rotates through the next 180°.

In this manner, both the fluence profile of the fan beam 26 and the attenuation of separate beam rays 47 between tumor slices 166, 167 can be made uniform along the length of a tumor 164 to eliminate irradiation gaps and irradiation hot spots.

VI. Imaging Confirmation Mechanism

As described above, the tomographic imaging system 63 operates to generate images used by the computer 61 and image reconstructor 69 to produce fluence profiles for every gantry angle φ and every translation table 11 position. In addition, the tomographic imaging system 63 may operate in tandem with the radiation source 32 to confirm the position of the radiation window 24 relative to the tumor. This position check can be used to limit irradiation dose errors either by correcting for patient position changes or by shutting down the machine.

During a therapy planning session, the tomographic imaging system 63 generates and stores raw x-ray attenuation data in the mass storage system 73. Because the table 11 is stationary as the tomographic imaging system 63 rotates about the tumor, the x-ray data generated by the system 63 will differ from that collected during a helical scan.

However, periodically, the helical scanning x-ray beam 29 and detector array 30 will produce data that should be identical to that employed in the therapy planning.

Figure 15E:
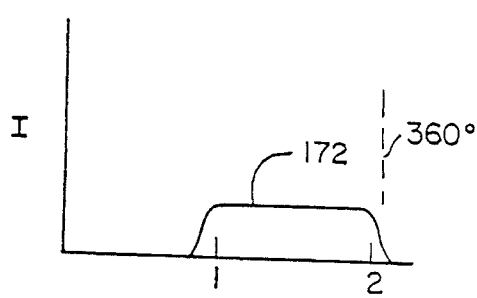

For example, referring to FIGS. 15(a) and 15(c), at the 180° rotation point, the irradiation window 172 is centered on the first slice 166 of the tumor 164. Similarly, referring to FIG. 15(e), the irradiation window 172 is also centered on a discrete slice, at the 360° rotation point. At these angles during a helical session, the raw data generated by the tomographic imaging system 63 should coincide with the x-ray data from the same angle generated for the specific slice during the tomographic imaging portion of the therapy planning session. These angles where data from the planning session and therapy session are identical are referred to herein as coincident angles.

Figure 17:
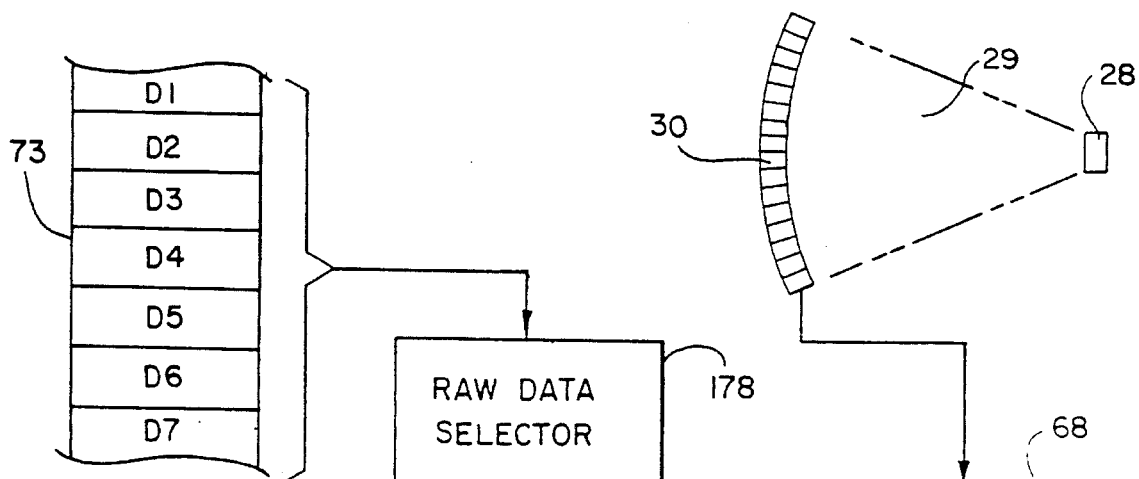
FIG. 17 is a block diagram depicting the motivating mechanism operation of the present invention.
Figure 17:
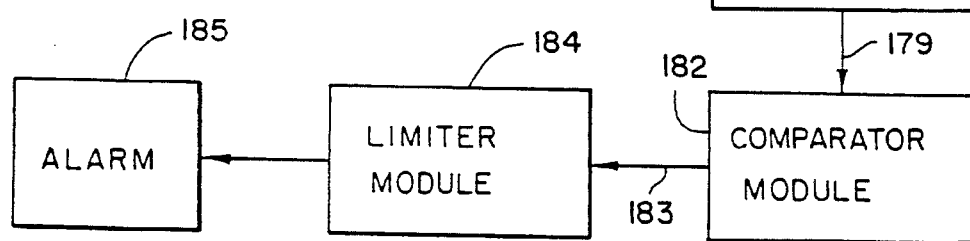

Referring to FIG. 17, the raw data generated during the planning session and stored in the mass storage unit 73 is downloaded into a raw data selector 178 which selects the data 180 corresponding to the anticipated coincidence angles. During the therapy session, the imaging source 28 and detector array 30 may cooperate to produce only the treatment data 179 necessary to make a position check, the data being generated at the anticipated coincidence angles (in FIGS. 15(c) and 15(e) at the 180° and 360° angles where the imaging beam 29 subtends a distinct tumor slice). A comparator module 182 can then correlate the selected data 180 with the treatment data 179 to generate a difference value 183 according to the following formula:

$$\text{Difference Value} = \sum_{k=1}^{n} |\psi(\rho, \phi_k) - \psi(t, \phi_k)| \qquad (16)$$

where n is the number of detector elements in the detector array, $\psi(\rho,\phi_k)$ is the flux detected at angle $\phi_k$ during the planning session and $\psi(t,\phi_k)$ is the flux detected at angle $\phi_k$ during the therapy session.

A limiter module 184 compares the difference value 183 to an acceptable limit. If the difference value 183 is not within the acceptable limit range, the limiter module produces an alarm signal. However, if the difference value 183 is not greater or less than the acceptable limit range, the limiter module 184 trips an alarm 185 to either shut down the radiation source or alert a therapist of possible patient movement.

The above description has been that of a preferred embodiment of the present invention. It will occur to those who practice the art that many modifications may be made without departing from the spirit and scope of the invention. For example, the therapy planning tomographic data may be generated in helical form to effect a more perfect match between that data and the imaging data collected during an irradiation session. Such data could be used to perform a constant position check on the patient and tumor during a therapy session, In addition, the x-ray source 28 and radiation source 32 may be configured so as to be in a single plane. In order to apprise the public of the various embodiments that may fall within the scope of the invention, the following claims are made:

We claim:

1. A radiation therapy machine for treating a patient having a treatment volume, the machine comprising:

a gantry for rotation with a gantry plane;

a radiation source disposed on the gantry for rotation with the gantry about an axis of rotation, the radiation source directing a radiation beam of a predetermined intensity appropriate to treat tumorous tissue toward the axis of rotation form a plurality of first gantry angles along the gantry plane;

an x-ray source disposed on the gantry for rotation with the gantry about the axis of rotation, the x-ray source for producing an x-ray beam directed toward the axis of rotation from a plurality of second gantry angles in a plane parallel to the gantry plane, the radiation source and the x-ray source positioned in separate parallel planes so that the radiation beam and x-ray beam do not intersect;

an x-ray detector disposed on the gantry and diametrically opposed to the x-ray source for receiving the x-ray beams therefrom and producing x-ray data; and a computer means for receiving the x-ray data and generating a tomographic image therefrom.

2. The radiation therapy machine as recited in claim 1 wherein the x-ray source is disposed on the gantry at a fixed and known gantry angle relative to the radiation source.

3. The radiation therapy machine as recited in claim 2 wherein the fixed and known gantry angle is 90°.

4. The radiation therapy machine as recited in claim 2 wherein the therapy machine is used with a table, the table is disposed along an axis of translation parallel to the axis of rotation for supporting a patient and for moving the patient along the axis of rotation while the radiation and x-ray sources are rotated around the axis of rotation, wherein, the x-ray source is offset from the gantry plane and offset by a gantry angle from the radiation source such that the radiation beam and x-ray beam sweep identical helical paths through the patient.

5. The radiation therapy machine as recited in claim 4 wherein the radiation source and x-ray source are positioned such that the x-ray source leads the radiation source in rotation around the patient.

* * * * *